United States Patent [19]

Engel

[11] Patent Number: 4,488,557

[45] Date of Patent: Dec. 18, 1984

[54] TOPICAL AGENT FOR TRANSCUTANEOUS MEASUREMENT OF PARTIAL PRESSURE OF OXYGEN

[76] Inventor: Rolf R. Engel, 3265 N. Snelling, Arden Hills, Minn. 55112

[21] Appl. No.: 585,774

[22] Filed: Mar. 2, 1984

[51] Int. Cl.³ .............................................. A61B 5/00
[52] U.S. Cl. .................................. 128/635; 128/639; 128/640; 128/641; 604/336; 604/892; 204/403; 424/275; 427/2
[58] Field of Search ....................... 128/635, 639–641; 604/336, 892; 204/403, 414, 431, 803; 424/275; 427/2

[56] References Cited

U.S. PATENT DOCUMENTS

| | | |
|---|---|---|
| 3,791,376 | 2/1974 | Rybak . |
| 4,224,125 | 9/1980 | Nakamura et al. . |
| 4,230,122 | 10/1980 | Lubbers et al. . |
| 4,265,250 | 5/1981 | Parker . |
| 4,274,418 | 6/1981 | Vesterager et al. . |
| 4,276,144 | 6/1981 | Hahn et al. . |
| 4,290,431 | 9/1981 | Herbert et al. . |
| 4,296,752 | 10/1981 | Welsh et al. . |
| 4,301,807 | 11/1981 | Mentelos . |
| 4,303,076 | 12/1981 | Danek . |
| 4,311,151 | 1/1982 | Hagihara . |

OTHER PUBLICATIONS

B. Nelson et al., "Effect of Thenoyltrifluoracetone on the Interaction of Succinate Dehydrogenase and Cytochrome b in Ubiquinone–Depleted Submitochondrial Particles", *Biochemical and Biophysical Research Communications*, vol. 44, No. 6, 1312–1320 (1971).

R. Ulvik et al., "Effect of Thenoyltrifluoracetone on Oxygen Consumption and Energy Conservation in Isolated Rat Liver Mitochondria", *FEBS Letters*, vol. 59, No. 2, 180–183 (North–Holland Publishing Company–Amsterdam, Nov. 1975).

P. Mowery et al., "Inhabition of Mammalian Succinate Dehydrogenase by Carboxins", *Archives of Biochemistry and Biophysics*, vol. 178, 495–506 (1977).

R. Ramsey et al., "Reaction site of carboxanilides and of thenoyltrifluoroacetone in complex II", *Proc. of Nat'l Academy of Sciences*, vol. 78, No. 2, 825–828 (Feb. 1981).

B. Trumpower et al., "Diminished Inhibition of Succinate-Cytochrome c Reductase Activity of Resolved Reductase Complex by Thenoyltrifluoroacetone in the Presence of Antimycin", *Biochemical and Biophysical Research Communications*, vol. 82, No. 1, 289–295 (1978).

K. Staron et al., "Different Sensitivity of Nuclear and Microsomal NADH–Cytochrome c Reductase Activities to Thenoyltrifluoroacetone", *FEBS Letters*, vol. 45, No. 1, 1–2 (North Holland Publishing Company–Amsterdam 1974).

M. Gutman et al., "Inhibition of Mitochondrial Malate Dehydrogenase by 2-thenoyltrifluoroacetone", *FEBS Letters*, vol. 49, No. 2, 170–173 (1974).

M. Gutman et al., "Distinction Between NAD and NADH-Binding Forms of Mitochondrial Malate Dehydrogenase as Shown by Inhibition with Thenoyltrifluoroacetone", *Biochimica et Biophysica Acta*, vol. 481, 33–41 (1977).

W. J. Ingledew et al., "The Probable Site of Action of Thenoyltrifluoroacetone on the Respiratory Chain", *Biochem. J.*, vol. 164, 617–620 (1977).

R. Engel et al., "The Effect of Topical Potassium Cyanide on Transcutaneous Gas Measurements", *Birth Defects: Original Article Series*, vol. 15, No. 4, 117–121 (The National Foundation 1979).

*Primary Examiner*—C. Fred Rosenbaum
*Assistant Examiner*—Edward J. Dalgewicz, III
*Attorney, Agent, or Firm*—Dorsey & Whitney

[57] ABSTRACT

The invention relates to a method for treating skin for assisting transcutaneous measurement of arterial partial pressure of oxygen. The method involves applying topically 2-thenoyltrifluoroacetone to the area of skin over which the partial pressure of oxygen is to be measured.

10 Claims, 8 Drawing Figures

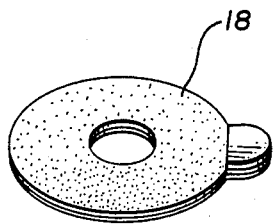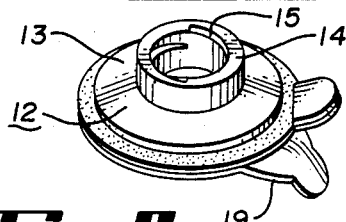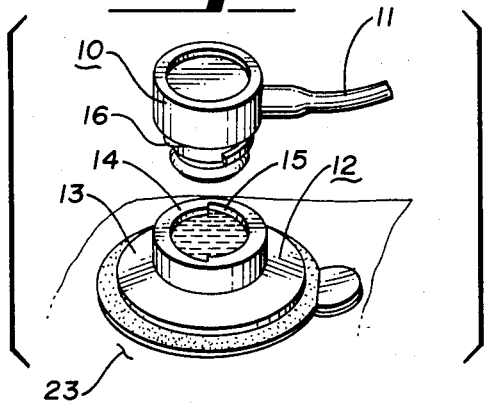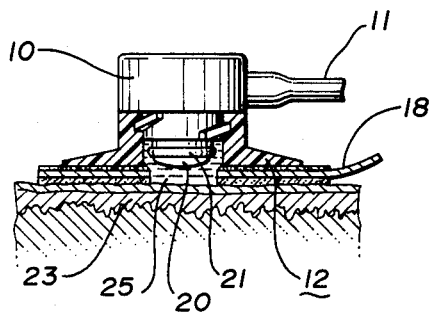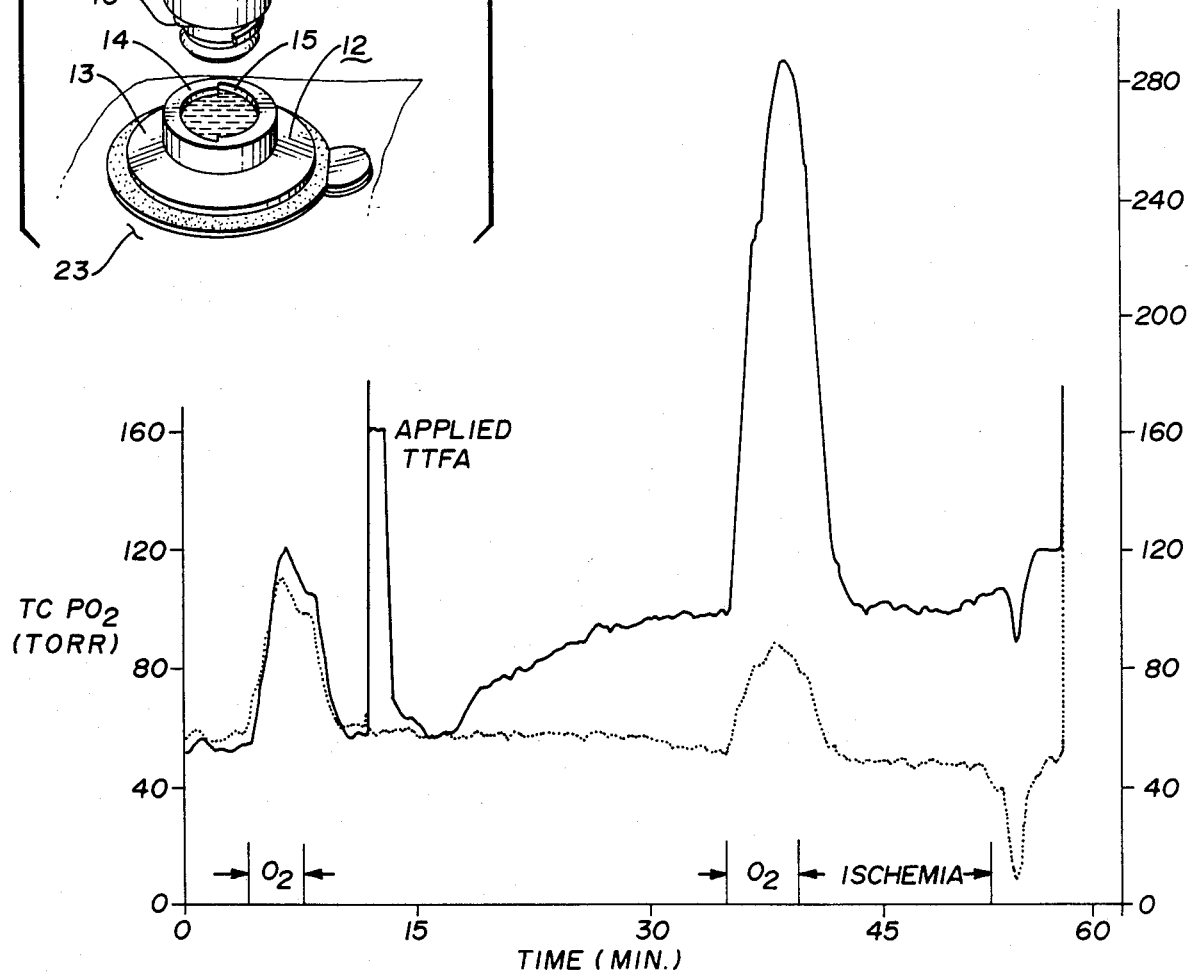

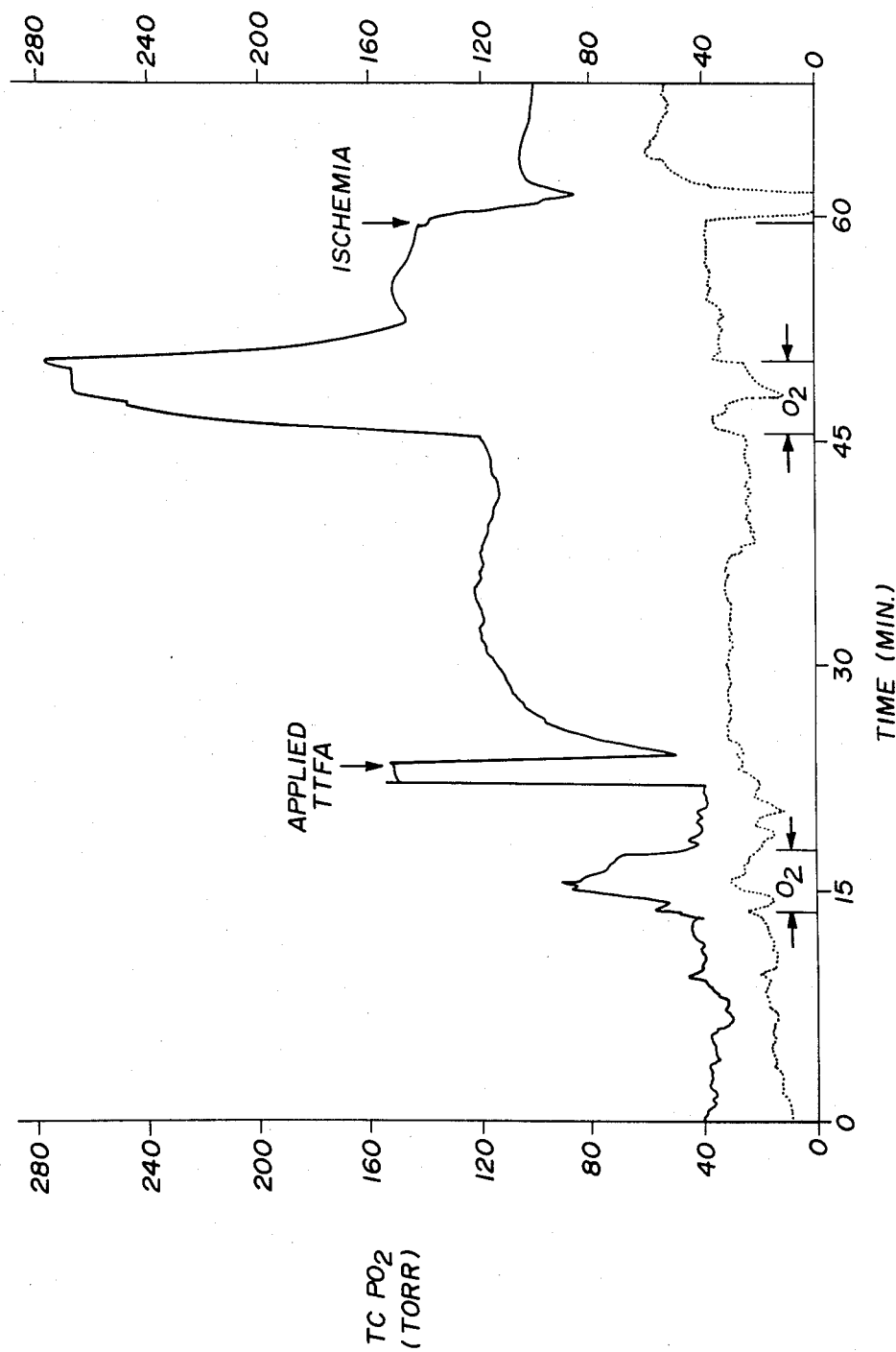

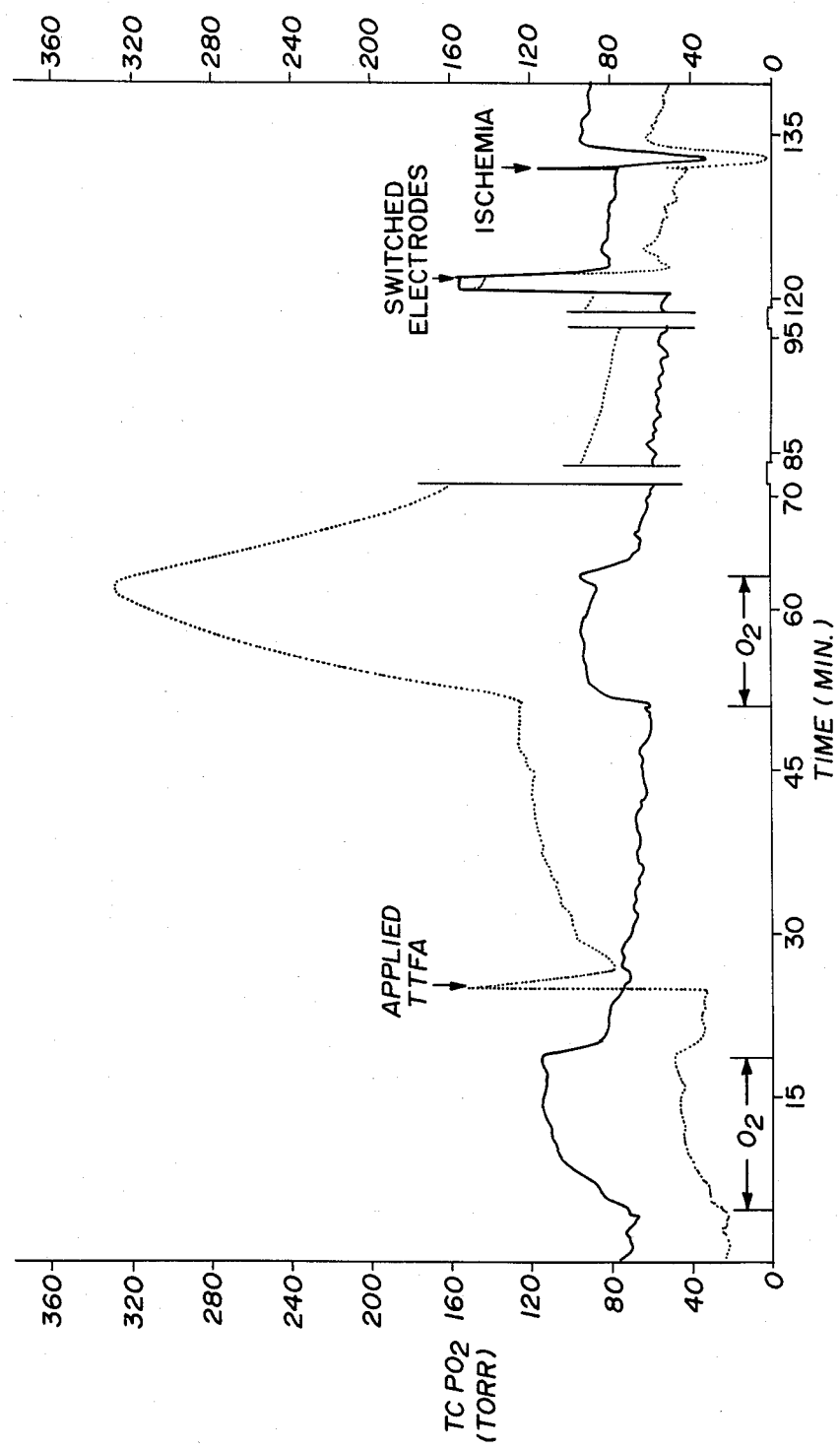

TOPICAL AGENT FOR TRANSCUTANEOUS MEASUREMENT OF PARTIAL PRESSURE OF OXYGEN

BACKGROUND OF THE INVENTION

1. Field of the Invention

This invention relates generally to transcutaneous measurement of partial pressure of oxygen and relates particularly to the use of 2-thenoyltrifluoroacetone as a topical agent for improving such measurements.

2. Description of the Prior Art

Transcutaneous oxygen monitors are available commercially (cf. TCM 2 by Radiometer A/S, Copenhagen, Denmark, $TCO_2M$ by Novametrix Medical Systems, Inc., Wallingford, Conn. 06492 and OXYMONITOR by Litton Medical Electronics, Elk Grove Village, Ill. 60007). These monitors utilize a sensor unit which is applied to the skin of a person whose transcutaneous partial pressure of oxygen is to be measured. The sensor unit generally comprises a barrier such as a membrane permeable to oxygen. Oxygen diffuses through the membrance and into an electrolyte solution stored on the electrode side of the membrane and in which oxygen is soluble. An electrode assembly in contact with the electrolyte solution measures the concentration of oxygen dissolved in the electrolyte solution, thus providing a measurement of the amount of oxygen diffusing through the skin. Alternative sensor units measure the quantity of oxygen diffusing through the skin without the use of membranes. Further alternatives perform such measurements without the use of electrodes.

Transcutaneous oxygen monitors are currently used in monitoring the transcutaneous partial pressure of oxygen in the prematurely born, both to guide treatment where supplemental oxygen is being administered and to assist in diagnosis where there is a question about the blood oxygen level. The transcutaneous partial pressure of oxygen and the diffusion of oxygen through the skin respond rapidly to changes in the concentration of inspired oxygen. Transcutaneous oxygen monitors are thus used frequently in treatment and diagnosis since too much oxygen can cause damage to a baby's retina and too little oxygen can cause brain damage.

The partial pressure of oxygen over the surface of skin does not correlate well with arterial partial pressure at normal skin temperatures. It is common to heat the skin by heating elements located in the sensor unit. Heating the skin in this manner has resulted in an acceptable correlation between arterial and transcutaneous partial pressures of oxygen in newborns. However, the recommended electrode temperature for newborns of 44° C. can produce thermal injury to skin after several hours. In an effort to reduce such thermal injury, sensor units are routinely relocated to a virgin patch of skin every several hours.

Transcutaneous oxygen monitors are also used in monitoring the transcutaneous partial pressure of oxygen in the diagnosis and treatment of various diseases in children and adults. The approach of heating the skin, even to an electrode temperature of 45° C., has not generally yielded an acceptable correlation between arterial and transcutaneous partial pressures of oxygen in children and adults.

It is an object of the present invention to reduce thermal injury to skin caused by heating the skin and to improve the correlation between arterial and transcutaneous partial pressures of oxygen. In particular it is an object of the present invention to achieve an acceptable correlation of arterial and transcutaneous partial pressures while using lower skin temperatures. It is an object to reduce thermal injury to skin and reduce the frequency with which sensor units must be relocated to virgin patches of skin. It is an object to achieve an acceptable correlation of arterial and transcutaneous partial pressures in adults as well as newborns.

SUMMARY OF THE INVENTION

The present invention provides a method for treating skin for assisting transcutaneous measurement of partial pressure of oxygen. The method comprises applying 2-thenoyltrifluoroacetone topically to an area of skin over which the partial pressure of oxygen is to be measured.

The 2-thenoyltrifluoroacetone may be in crystalline form and applied directly to the area of skin over which the partial pressure of oxygen is to be measured. The amount of 2-thenoyltrifluoroacetone crystals applied topically is about 5 mg or less. The 2-thenoyltrifluoroacetone may be dissolved or suspended in a liquid medium prior to topical application. The amount of 2-thenoyltrifluoroacetone in the liquid medium in the case of the preferred embodiment is about 2% to about 3% by weight. The liquid medium may comprise a contact gel, which in its preferred form may comprise water and glycerol. Propylene glycol may be a further constituent of the contact gel.

The present invention further provides a method for transcutaneous measurement of partial pressure of oxygen comprising applying 2-thenoyltrifluoroacetone topically to an area of skin over which the partial pressure of oxygen is to be measured, placing a sensor unit over the area of skin to which the 2-thenoyltrifluoroacetone has been applied and sealing the area of skin from the ambient atmosphere, raising the temperature of the area of skin by heat emanating from the sensor unit, and measuring with the sensor unit the partial pressure of oxygen over the area of skin. The 2-thenoyltrifluoroacetone may be in crystalline form or dissolved or suspended in a liquid medium in the amounts set forth above. The liquid medium may comprise contact gel for use between the area of skin and a membrane, the membrane separating sensor electrodes from the skin. The contact gel may be composed as set forth above.

The present invention further provides for a topical agent for assisting transcutaneous measurement of partial pressure of oxygen comprising 2-thenoyltrifluoroacetone, in an amount about 2% to about 3% by weight, dissolved or suspended in a liquid medium. The liquid medium may comprise a contact gel which may comprise water and glycerol. The contact gel may further comprise propylene glycol.

BRIEF DESCRIPTION OF THE DRAWINGS

FIG. 1 shows a double-sided adhesive ring showing adhesive exposed on the topside.

FIG. 2 shows a mounting ring forming part of a transcutaneous oxygen monitor and an adhesive ring attached thereto by its top adhesive surface.

FIG. 3 shows a sensor unit which is about to be mounted on the mounting ring, said mounting ring adhering to a patient's skin by virtue of the adhesive ring.

FIG. 4 shows a side view and partial sectional view of the sensor unit shown in FIG. 3, the sensor unit being fully mounted on the mounting ring.

FIG. 5 shows transcutaneous measurements on the forearm of an adult male after topical application of 2-thenoyltrifluoroacetone mixed with contact gel (solid line) in comparison with similar measurements without topical application of 2-thenoyltrifluoroacetone (dotted line).

FIG. 6 shows transcutaneous measurements on the back of a rabbit after topical application of 2-thenoyltrifluoroacetone mixed with contact gel (solid line) in comparison with such measurements without topical application of 2-thenoyltrifluoroacetone (dotted line).

FIG. 7 shows transcutaneous measurements on the abdomen of a rat after topical application of 2-thenoyltrifluoroacetone mixed with contact gel (dotted line) in comparison with such measurements without topical application of 2-thenoyltrifluoroacetone (solid line); the two sensor units being reversed at 123 minutes.

DESCRIPTION OF THE PREFERRED EMBODIMENT

Figure 8:
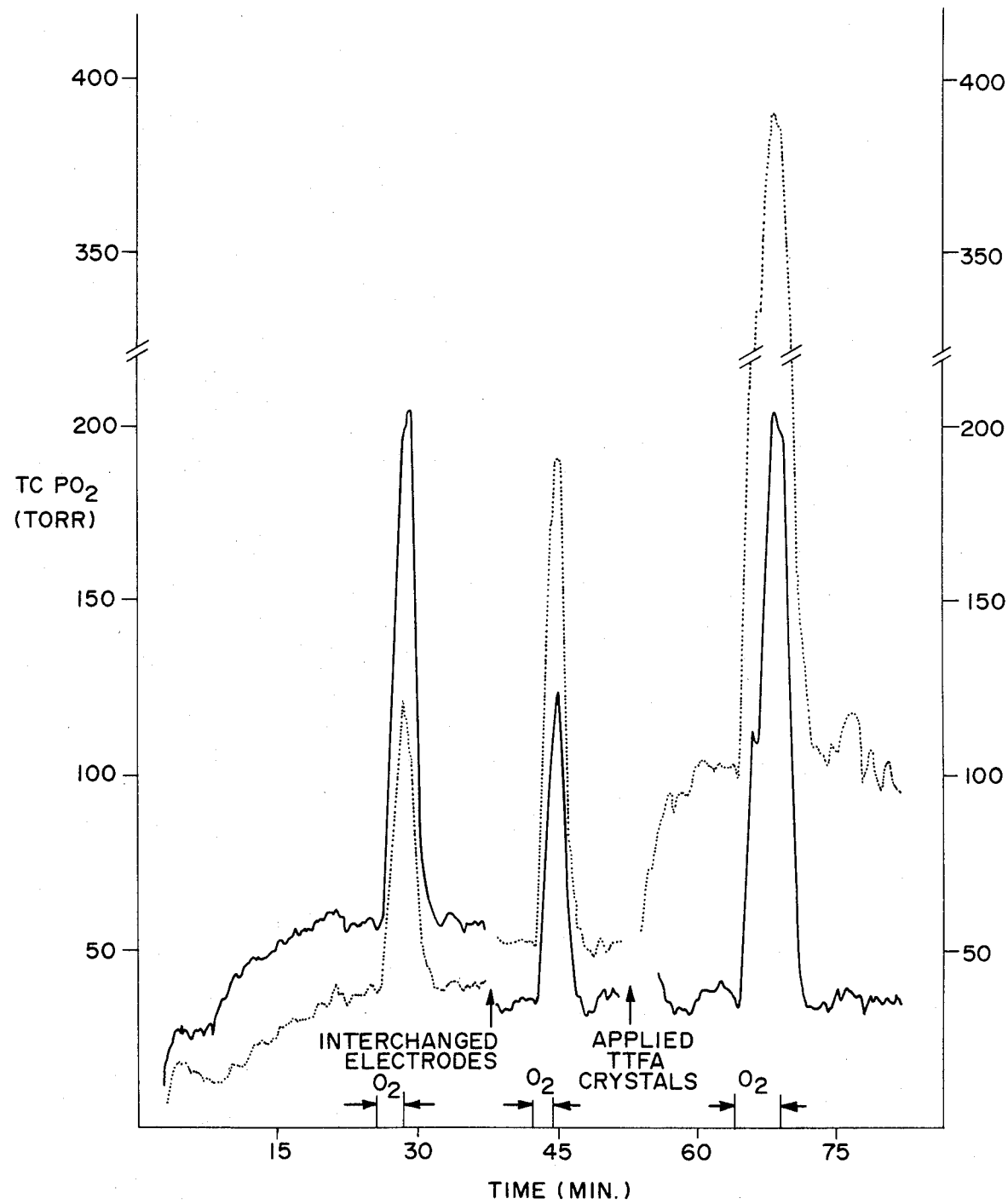
FIG. 8 shows transcutaneous measurements on the forearm of an adult male after topical application at point A of 2-thenoyltrifluoroacetone crystals in comparison with similar measurements without such topical application, leads to the sensor units being reversed at point B.

In its preferred embodiment, the methods and topical agents of the present invention are used in conjunction with existing transcutaneous oxygen monitors. These oxygen monitors are available commercially as TCM 2 by Radiometer A/S, Copenhagen, Denmark, TCO₂M by Novametrix Medical Systems, Inc., Wallingford, Conn. 06492 and as OXYMONITOR by Litton Medical Electronics, Elk Grove Village, Ill. 60007. Suitable transcutaneous oxygen monitors are described in U.S. Pat. No. 4,274,418, issued June 23, 1981 to Vesterager, et al., U.S. Pat. No. 4,324,256, issued Apr. 13, 1982, to Vesterager, U.S. Pat. No. 4,301,807, issued Nov. 24, 1981 to Mentelos, U.S. Pat. No. 4,265,250, issued May 5, 1981 to Parker, U.S. Pat. No. 4,296,752, issued Oct. 27, 1981 to Welsh et al., U.S. Pat. No. 4,311,151, issued Jan. 19, 1982 to Hagihara, U.S. Pat. No. 4,290,431 issued Sept. 22, 1981 to Herbert et al., and U.S. Pat. No. 4,303,076, issued Dec. 1, 1981 to Danek, which are incorporated in their entirety herein by reference thereto.

The above transcutaneous oxygen monitor by Radiometer may be described with reference to FIGS. 1–4. Sensor unit 10 may be electrically connected to suitable measuring and registering units (not shown) by means of cable 11. Sensor unit 10 is used in connection with mounting ring 12 having a substantially radially extending flange 13 forming a skin abutment surface, and a substantially axially extending power or neck 14 with an internal thread 15 adapted to cooperate with a thread 16 formed on sensor unit 10 for releasably connecting sensor unit 10 to mounting ring 12. Mounting ring 12 may be fastened to the skin by means of an adhesive ring 18 which is provided with adhesives on both sides. Such adhesive rings 18 may be arranged on a sheet or foil (not shown) serving as a protecting sheet for the adhesive layer on one side of the rings. When the mounting ring is to be fastened onto a patient's skin adhesive ring 17 is removed from the sheet so that the adhesive layer on one side of the ring becomes exposed. Adhesive ring 18 may be mounted onto mounting ring 12 with the exposed adhesive layer facing the skin abutment surface of flange 13. Protective layer 19 on the other side of ring 17 is then removed. Mounting ring 12 may then be adhered to a selected area of skin of a patient and sensor unit 10 may thereafter be mounted on mounting ring 12 by means of the threaded connections 15 and 16.

Sensor unit 10 may be of a type having a permeable membrane 20 mounted by means of an elastic ring 21. When sensor unit 10 is mounted, membrane 20 extends into the annular mounting ring 12 to such an extent that membrane 8 is positioned above the surface of skin 23 shown in FIG. 4. Membrane 8, skin surface 23, and the surrounding inner wall of mounting ring 12 define a sealed measuring chamber which is preferably filled with a contact gel 25.

Gases, such as oxygen and carbon dioxide, will diffuse from blood vessels of a patient through the skin tissue and into the measuring chamber. Gases diffuse through membrane 8 into an electrolyte solution stored on the electrode side of membrane 8 and in which oxygen is soluble. An electrode assembly (not shown) in contact with the electrolyte solution measures the concentration of oxygen dissolved in the electrolyte solution, thus providing a measurement of the amount of oxygen diffusing through the skin. Sensor unit 10, communicating with the measuring chamber through semipermeable membrane 8, may continuously monitor the partial pressure of these gases.

Skin is heated by heating elements located in a sensor unit. Heat is conducted through the electrolyte solution, the permeable membrane 8, and contact gel 25, thereby heating skin 23. Applicant believes that heating skin in this manner causes vasodilation and a shift in the hemoglobin-oxygen dissociation curve with the result that excess oxygen released by the heating tends to compensate for the fraction believed to be consumed by the skin. In order to arrive at a suitable correlation between transcutaneous and arterial partial pressure of oxygen in adults as well as newborns and at lowered skin temperatures, 2-thenoyltrifluoroacetone was added to the contact gel as follows.

2-thenoyltrifluoroacetone crystals, available commercially from Sigma Chemical Co., St. Louis, Mo. 63172, were stored below 0° C. in order to preserve their activity. Contact gel, available commercially as S43716 from Radiometer America Inc., Westlake, Ohio 44145, was composed in grams per kilogram of contact gel as follows: disodium hydrogenphosphate dihydrate 9.30 g; potassium dihydrogen phosphate 1.79 g.; sodium chloride 9.03 g.; glycerol 489 g.; deionized water 489 g.; and the germicides methyl-4-hydroxybenzoate and propyl-4-hydroxy-benzoate. 2-thenoyltrifluoroacetone crystals, stored at less than 0° C., were ground up with a mortar and pestel into a fine powder immediately prior to the following mixing. The freshly powdered 2-thenoyltrifluoroacetone was mixed with propylene glycol. An amount of contact gel equal in volume to the propylene glycol was added forming a propylene glycol/contact gel mixture, having a concentration of 2-thenoyltrifluoroacetone of about 2% by weight.

After fastening a mounting ring 12 to skin with a double adhesive ring 18, approximately three drops of the contact gel/propylene glycol mixture containing about 2% 2-thenoyltrifluoroacetone were placed in the center well of the mounting ring. A sensor unit was screwed into the mounting ring and any trapped air was displaced by the layer of contact gel/propylene glycol mixture, the excess liquid pouring over the top of the mounting ring. Sensor units used were those commercially available as TCM-2 by Radiometer and TCO$_2$M by Novametrix Medical Systems, Inc.

EXAMPLE 1

Two sensor units were heated to a temperature of 42° C. and attached to the forearm of an adult male according to the above discussed procedures. In the absence of 2-thenoyltrifluoroacetone, the sensor units showed a similar elevation in the partial pressure of oxygen from about 50 TORR to about 120 TORR upon the subject breathing oxygen. At the 13 minute mark in FIG. 5, the above described contact gel/propylene glycol mixture containing 2% by weight of 2-thenoyltrifluoroacetone was applied topically to the skin beneath one sensor (the "active" sensor represented by solid line in FIG. 5) but not to the other sensor (the "control" sensor represented by dotted line in FIG. 5). While the subject was breathing room air, the partial pressure of oxygen measured by the active sensor rose from about 65 TORR to about 95 TORR as the 2-thenoyltrifluoroacetone took effect. The partial pressure measured by the control sensor remained steady at about 65 TORR while the subject breathed room air. Upon breathing oxygen, the partial pressure measured by the active sensor rose from about 95 TORR to over 280 TORR while the partial pressure measured by the control sensor rose from about 50 TORR to about 85 TORR. Thus, the topical application of 2-thenoyltrifluoroacetone resulted in a pronounced rise in transcutaneous partial pressure of oxygen for inhalation of room air and inhalation of pure oxygen. Similarly, as shown in FIG. 5, a pronounced fall in the transcutaneous partial pressure of oxygen occurs during ischemia. The above effects of 2-thenoyltrifluoroacetone continued for at least several hours.

Thus, the topical application of 2-thenoyltrifluoroacetone in conjunction with the above commercial monitors operating at a sensor temperature of 42° C. resulted in a transcutaneous partial pressure of oxygen approximately equal to the 95 TORR partial pressure of oxygen we would expect to find in that subject's arterial blood. A correlation between arterial and transcutaneous partial pressure of oxygen was obtained at 42° C. for the normal subject in FIG. 5. This illustrates that a correlation can be obtained at temperatures less than the 44° C. for newborns and 45° C. for adults presently recommended in connection with the commercially available sensor units.

EXAMPLE 2

FIG. 6 shows that the topical application of the above contact gel/propylene glycol mixture containing about 2% by weight 2-thenoyltrifluoroacetone to the back of a rabbit resulted in a pronounced rise in the transcutaneous partial pressure of oxygen for both the breathing of room air and inhalation of pure oxygen when compared to a control tracing (dotted line).

EXAMPLE 3

FIG. 7 shows that the topical application of the above contact gel/propylene glycol mixture containing about 2% by weight 2-thenoyltrifluoroacetone to the abdomen of a rat resulted in a pronounced rise in the transcutaneous partial pressure of oxygen for both the breathing of room air and inhalation of pure oxygen when compared to a control tracing (solid line). At 123 minutes, the two sensor units were reversed to demonstrate that the differences between the sensor unit and the control were attributable to the topical application of 2-thenoyltrifluoroacetone. Results similar to these in Examples 1-3, i.e. a correlation between arterial and transcutaneous partial pressure of oxygen, were obtained in this example by using 3% by weight 2-thenoyltrifluoroacetone in the above contact gel/propylene glycol mixture.

DESCRIPTION OF ALTERNATIVE EMBODIMENTS 2-thenoyltrifluoroacetone may be dissolved or suspended in liquid media other than the particular contact gel/propylene glycol mixture suggested above. Moreover, 2-thenoyltrifluoroacetone may be used in conjunction with transcutaneous oxygen monitors other than those set forth above. Some prior art monitors do not utilize a permeable membrane. Instead, sensing electrodes are separated from the skin area by an electrolyte solution only (cf. Osborne, et al., "The Design and Construction of a Transcutaneous Oxygen Electrode Requiring No Diffusion Membrane" published in CONTINUOUS TRANSCUTANEOUS BLOOD MONITORING (Edited by Huch et al., published by Marcel Dekker, Inc., New York 1983) at pages 117-122.). Such an electrolyte solution containing 2-thenoyltrifluoroacetone would be an effective topical agent for such membrane-free transcutaneous oxygen monitors. Use of this topical agent would allow lowering the temperature of the sensor electrodes and enhance a correlation between arterial and transcutaneous partial pressure measurements in adults as well as newborns.

2-thenoyltrifluoroacetone may be used as a topical agent in a form other than dissolved or suspended in a liquid medium. 2-thenoyltrifluoroacetone may be applied directly to the skin in crystaline form. Other delivery media for topical application of 2-thenoyltrifluoroacetone may include a gelatinous base or solid matrix or other medium which may release the 2-thenoyltrifluoroacetone over an extended period or all at once. This is illustrated by the following example.

EXAMPLE 4

About 5 mg of 2-thenoyltrifluoroacetone in crystalline form were applied directly to the skin inside the well of a mounting ring, followed by the addition of commercial contact gel available as S43716 from Radiometer. FIG. 8 shows that the application of crystalline 2-thenoyltrifluoroacetone to the forearm of an adult male resulted in a pronounced rise in the transcutaneous partial pressure of oxygen for both inhalation of room air and inhalation of pure oxygen when compared to a control.

The foregoing Examples illustrate that the above concentrations and quantities of 2-thenoyltrifluoroacetone will result in a correlation between arterial and transcutaneous partial pressures while operating commercially available oxygen monitors at sensor temperatures lower than heretofore possible. It will be clear to persons knowledgeable in the art that other concentrations or quantities of 2-thenoyltrifluoroacetone than these disclosed will allow achieving a correlation of arterial and transcutaneous partial pressures for other types of oxygen monitors now existing or developed in the future. The effect of 2-thenoyltrifluoroacetone is believed to result from inhibition of cutaneous oxygen consumption, thereby allowing a wide-range of methods and modes of topical application.

While the invention has been described in connection with specific preferred and alternative embodiments, it will be understood that it is capable of further modifications and this application is intended to cover any variations, uses, or adaptations of the use of 2-thenoyltrifluoroacetone within the scope of the appended claims:

I claim:

1. A method for transcutaneous measurement of arterial partial pressure of oxygen comprising:

applying topically 2-thenoyltrifluoroacetone to an area of skin over which the partial pressure of oxygen is to be measured;

placing a sensor unit over the area of skin to which the 2-thenoyltrifluoroacetone has been applied and sealing the area of skin from the ambient atmosphere;

raising the temperature of the area of skin by heat emanating from the sensor unit; and measuring with the sensor unit the transcutaneous partial pressure of oxygen over the area of skin.

2. The method of claim 1 wherein the 2-thenoyltrifluoroacetone is in crystalline form and is applied directly to the area of skin over which the partial pressure of oxygen is to be measured.

3. The method of claim 2 wherein the amount of 2-thenoyltrifluoroacetone crystals is about 5 mg or less.

4. The method of claim 1 wherein the 2-thenoyltrifluoroacetone is embodied in a gelatinous or solid matrix delivery medium.

5. The method of claim 1 wherein the 2-thenoyltrifluoroacetone is dissolved or suspended in a liquid medium prior to topical application.

6. The method of claim 5 wherein the amount of 2-thenoyltrifluoroacetone in the liquid medium is in the range of about 2% to about 3% by weight.

7. The method of claim 6 wherein the amount of 2-thenoyltrifluoroacetone in the liquid medium is about 2% by weight.

8. The method of claim 5 wherein the liquid medium further comprises contact gel for use between the area of skin and a membrane, the membrane separating sensor electrodes from the skin.

9. The method of claim 8 wherein the contact gel comprises water and glycerol.

10. The method of claim 9 wherein the liquid medium further comprises propylene glycol.